(12) United States Patent
Mailloux et al.

(10) Patent No.: US 9,033,958 B2
(45) Date of Patent: May 19, 2015

(54) SURGICAL ROBOTIC SYSTEM

(75) Inventors: Pierre Mailloux, La Celle St-Cloud (FR); Christopher Plaskos, New York, NY (US)

(73) Assignee: Perception Raisonnement Action en Medecine, La Tronche (FR)

( * ) Notice: Subject to any disclaimer, the term of this patent is extended or adjusted under 35 U.S.C. 154(b) by 954 days.

(21) Appl. No.: 12/616,575

(22) Filed: Nov. 11, 2009

(65) Prior Publication Data
US 2010/0130986 A1 May 27, 2010

Related U.S. Application Data

(60) Provisional application No. 61/113,500, filed on Nov. 11, 2008.

(51) Int. Cl.
*A61B 19/00* (2006.01)

(52) U.S. Cl.
CPC ..... *A61B 19/2203* (2013.01); *A61B 2019/4868* (2013.01)

(58) Field of Classification Search
USPC ............................................................ 606/1
See application file for complete search history.

(56) References Cited

U.S. PATENT DOCUMENTS

| | | | |
|---|---|---|---|
| 4,457,307 A | 7/1984 | Stillwell | |
| 4,574,794 A | 3/1986 | Cooke et al. | |
| 5,228,459 A | 7/1993 | Caspari et al. | |
| 5,417,695 A | 5/1995 | Axelson, Jr. | |
| 5,454,816 A | 10/1995 | Ashby | |
| 5,474,559 A | 12/1995 | Bertin et al. | |
| 5,571,110 A | 11/1996 | Matsen et al. | |
| 5,601,563 A | 2/1997 | Burke et al. | |
| 5,653,714 A | 8/1997 | Dietz et al. | |
| 5,682,886 A | 11/1997 | Delp et al. | |
| 5,683,397 A | 11/1997 | Vendrely et al. | |
| 5,710,870 A * | 1/1998 | Ohm et al. ................... | 700/263 |
| 5,769,855 A | 6/1998 | Bertin et al. | |
| 5,806,518 A | 9/1998 | Mittelstadt | |
| 5,817,097 A | 10/1998 | Howard et al. | |
| 5,824,085 A | 10/1998 | Sahay et al. | |
| 5,860,981 A | 1/1999 | Bertin et al. | |
| 5,916,231 A * | 6/1999 | Bays ............................. | 606/180 |
| 6,056,754 A | 5/2000 | Haines et al. | |

(Continued)

FOREIGN PATENT DOCUMENTS

| | | |
|---|---|---|
| CA | 2219190 A1 | 11/1996 |
| CA | 2376019 A1 | 1/2001 |

(Continued)

OTHER PUBLICATIONS

Office Action issued Feb. 27, 2009 in U.S. Appl. No. 11/305,887.

(Continued)

*Primary Examiner* — Lynsey Crandall
(74) *Attorney, Agent, or Firm* — Kim Winston LLP

(57) ABSTRACT

In one embodiment, a surgical robotic system includes a main controller and a motor unit assembly that is associated with a robot and is in communication with the main controller. The motor unit assembly has a non-sterile motor unit and a sterile enclosure that surrounds and contains the motor unit. The motor unit includes at least one motor and a motor controller that is operatively connected to the motor unit, wherein the motor unit and the enclosure are configured to permit attachment between the motor unit and the controller.

30 Claims, 6 Drawing Sheets

(56) References Cited

U.S. PATENT DOCUMENTS

| | | | |
|---|---|---|---|
| 6,132,368 A * | 10/2000 | Cooper | 600/102 |
| 6,226,548 B1 | 5/2001 | Foley et al. | |
| 6,527,443 B1 | 3/2003 | Vilsmeier et al. | |
| 6,554,837 B1 | 4/2003 | Hauri et al. | |
| 6,558,391 B2 | 5/2003 | Axelson, Jr. et al. | |
| 6,575,980 B1 | 6/2003 | Robie et al. | |
| 6,685,711 B2 | 2/2004 | Axelson, Jr. et al. | |
| 6,702,821 B2 | 3/2004 | Bonutti | |
| 6,712,824 B2 | 3/2004 | Millard et al. | |
| 6,738,656 B1 | 5/2004 | Ferre et al. | |
| 6,858,032 B2 | 2/2005 | Chow et al. | |
| 7,029,477 B2 | 4/2006 | Grimm | |
| 7,488,324 B1 | 2/2009 | Metzger et al. | |
| 7,520,880 B2 | 4/2009 | Claypool et al. | |
| 7,547,307 B2 | 6/2009 | Carson et al. | |
| 7,569,060 B2 | 8/2009 | Faoro | |
| 8,096,997 B2 | 1/2012 | Plaskos et al. | |
| 8,126,533 B2 | 2/2012 | Lavallee | |
| 8,282,646 B2 | 10/2012 | Schoenefeld et al. | |
| 2004/0039396 A1 | 2/2004 | Couture et al. | |
| 2004/0127788 A1 | 7/2004 | Arata | |
| 2004/0172138 A1 | 9/2004 | May et al. | |
| 2004/0221625 A1 * | 11/2004 | Aouad | 68/17 R |
| 2005/0055028 A1 | 3/2005 | Haines | |
| 2005/0101966 A1 | 5/2005 | Lavallee | |
| 2005/0234435 A1 * | 10/2005 | Layer | 606/1 |
| 2006/0015114 A1 | 1/2006 | Bernardoni et al. | |
| 2006/0052791 A1 | 3/2006 | Hagen et al. | |
| 2006/0161052 A1 | 7/2006 | Colombet et al. | |
| 2006/0200161 A1 | 9/2006 | Plaskos et al. | |
| 2007/0106128 A1 | 5/2007 | Lavallee | |
| 2007/0185498 A2 | 8/2007 | Lavallee | |
| 2008/0004481 A1 * | 1/2008 | Bax et al. | 600/7 |
| 2008/0243127 A1 | 10/2008 | Lang et al. | |
| 2009/0018445 A1 | 1/2009 | Schers et al. | |
| 2009/0024142 A1 * | 1/2009 | Ruiz Morales | 606/130 |
| 2009/0228016 A1 | 9/2009 | Alvarez | |
| 2010/0130986 A1 | 5/2010 | Mailloux et al. | |
| 2010/0256504 A1 | 10/2010 | Moreau-Gaudry et al. | |
| 2010/0268240 A1 | 10/2010 | McGinley et al. | |
| 2011/0071530 A1 | 3/2011 | Carson | |
| 2011/0130761 A1 | 6/2011 | Plaskos et al. | |

FOREIGN PATENT DOCUMENTS

| | | |
|---|---|---|
| DE | 20303643 U1 | 7/2003 |
| FR | 2856268 A1 | 12/2004 |
| WO | 9832384 A1 | 7/1998 |
| WO | 9960939 | 12/1999 |
| WO | 2004112620 A1 | 12/2004 |
| WO | WO2006106419 | 10/2006 |

OTHER PUBLICATIONS

Office Action issued Nov. 13, 2009 in U.S. Appl. No. 11/305,887.

Int'l Search Report issued Sep. 29, 2006 in Int'l Application No. PCT/IB2006/000806; Written Opinion.

Int'l Preliminary Report on Patentability issued Oct. 9, 2007 in Int'l Application No. PCT/IB2006/000806; Written Opinion.

"Building a complete surface model from sparse data using statistical shape models: application to computer assisted knee surgery" by M. Fluete and S. Lavallée, published in Medical Image Computing and Computer-Assisted Intervention—MICCAI'98, Spinger-Verlag LNCS Series, pp. 880-887, Oct. 1998.

Fleute M, Lavallee S, Julliard R. Incorporating a statistically based shape model into a system for computer-assisted anterior cruciate ligament surgery. Medical Image Analysis. Sep. 1999; 3(3):209-22.

Cobb J, Henckel J, Gomes P, et al, Hands-on robotic unicompartmental knee replacement, Journal of Bone and Joint Surgery—British Volume, 2006, vol. 88, pp. 188-197, ISSN: 0301-620X.

Jakopec M, Harris SJ, Rodriguez Y Baena F, et al , The first clinical application of a 'Hands-On' robotic knee surgery system, Computer Aided Surgery, 2001, vol. 6, pp. 329-339, ISSN: 1092-9088.

Office Action issued Apr. 22, 2013 in U.S. Appl. No. 11/908,449.

Office Action issued Nov. 8, 2013 in U.S. Appl. No. 11/908,449.

Office Action issued Sep. 9, 2014 in U.S. Appl. No. 13/524,424.

Office Action issued Oct. 9, 2014 in U.S. Appl. No. 11/908,449.

* cited by examiner

SURGICAL ROBOTIC SYSTEM

CROSS-REFERENCE TO RELATED APPLICATION

The present application claims the benefit of U.S. Patent Application No. 61/113,500, filed Nov. 11, 2008, which is hereby incorporated by reference in its entirety.

TECHNICAL FIELD

This invention relates to robotic assisted surgery, and in particular robotic positioning systems for use in computer assisted surgery and sterile surgical environments, such as in the operating room.

BACKGROUND

Surgery requires a sterile environment, free of bacteria which can cause infection in the surgical wound and sepsis.

Many surgical procedures also require a high precision in the surgical gesture. For example, in joint replacement or resurfacing surgery, such as in the knee and hip, it is important to implant the artificial joint with certain accuracy with respect to several possible criteria, including alignment to the skeleton, and to the soft tissues surrounding the joint.

The requirement of high accuracy in surgery has led to the introduction of computer and robotic assisted surgical systems (CAS) in the operating room. The following references describe some surgical robotic systems known in the art: PI Galileo (Plus Orthopaedics, Smith and Nephew), iBlock/Praxiteles (Praxim), Robodoc (Integrated Surgical Systems), MAKO Surgical Corp, The Acrobot Surgical System, da Vinci Surgical System (Intuitive Surgical, Inc.). Robotic surgical systems typically have to interact with both the patient and the surgeon in the operating theatre, and therefore they need to be sterile and not contaminate the surgical field. Some robotic systems are steralizible in conventional autoclave systems. Other systems that are not convenient or practical to sterilize are usually covered with a sterile drape to prevent microbes from contaminating the surgical field. This can be problematic however because the drape application procedure can be technically complex and require proper training and practice in order to assure that the sterile zone is not compromised during the draping process.

Robotic systems also need to be accurate, safe and reliable. They need to function as predicted and be dependable, and not be susceptible to electromagnetic noise, long use, or the sterilization and cleaning processes commonly required for surgical equipment.

It is an object of this invention to provide a robotic positioning system that is highly reliable and can be used in a sterile environment.

It is an object of this invention to provide a robotic positioning system that can be enclosed in an enclosure assembly that is simple to manufacture and can be either sterilizable or provided as single use.

SUMMARY

In one embodiment, a surgical robotic system includes a main controller and a motor unit assembly that is associated with a robot and is in communication with the main controller. The motor unit assembly has a non-sterile motor unit and a sterile enclosure that surrounds and contains the motor unit. The motor unit includes at least one motor and a motor controller that is operatively connected to the motor unit, wherein the motor unit and the enclosure are configured to permit attachment between the motor unit and the controller. In one embodiment, the enclosure is formed of two parts that are detachable from one another in which each part includes a sterile outer surface, while an inner surface of each part is non-sterile due to the presence of the non-sterile motor unit. The first part is a hollow enclosure base that receives the motor unit and include a first seal member at one end thereof, the second part being an enclosure cover that mates with the enclosure base for capturing the motor unit therebetween. The enclosure cover has a second seal member that mates with the first seal member for providing a seal. The motor unit includes a pair of motors each of which has a drive shaft and the enclosure includes a pair of output shafts that are coupled to the drive shaft of the motors when the motor unit is in a fully assembled position within the enclosure.

In another embodiment, a process for assembling a motor unit assembly that is associated with a surgical robotic system in an aseptic transfer process comprising the steps of: (a) sterilizing an insertion guide, an enclosure base and an enclosure cover that is complementary to the enclosure base, wherein the motor unit is in a non-sterile condition, the enclosure base having an opening that forms an entrance into a hollow interior space; (b) coupling the insertion guide to the enclosure base while maintaining the insertion guide and enclosure base in a sterile condition, the insertion guide having an opening that is axially aligned with the opening of the enclosure base; (c) inserting the motor unit into the hollow interior space by passing it through the opening of the insertion guide; (d) removing the insertion guide off of the enclosure base and from the sterile field that includes the enclosure base and cover; and (e) coupling the enclosure cover to the enclosure base with the motor unit being sealingly contained therebetween. The motor unit includes at least one motor and a motor controller that is operatively connected to the motor unit and fully contained within the sealed enclosure surrounding the motor unit, wherein the motor unit and the enclosure are configured to permit attachment between the motor unit and a main controller. The motor unit also includes a drive train, output shafts and support bearing for supporting the output shafts, thereby providing precise output positioning capabilities.

BRIEF DESCRIPTION OF THE DRAWING FIGURES

DETAILED DESCRIPTION OF EMBODIMENTS

Figure 1:
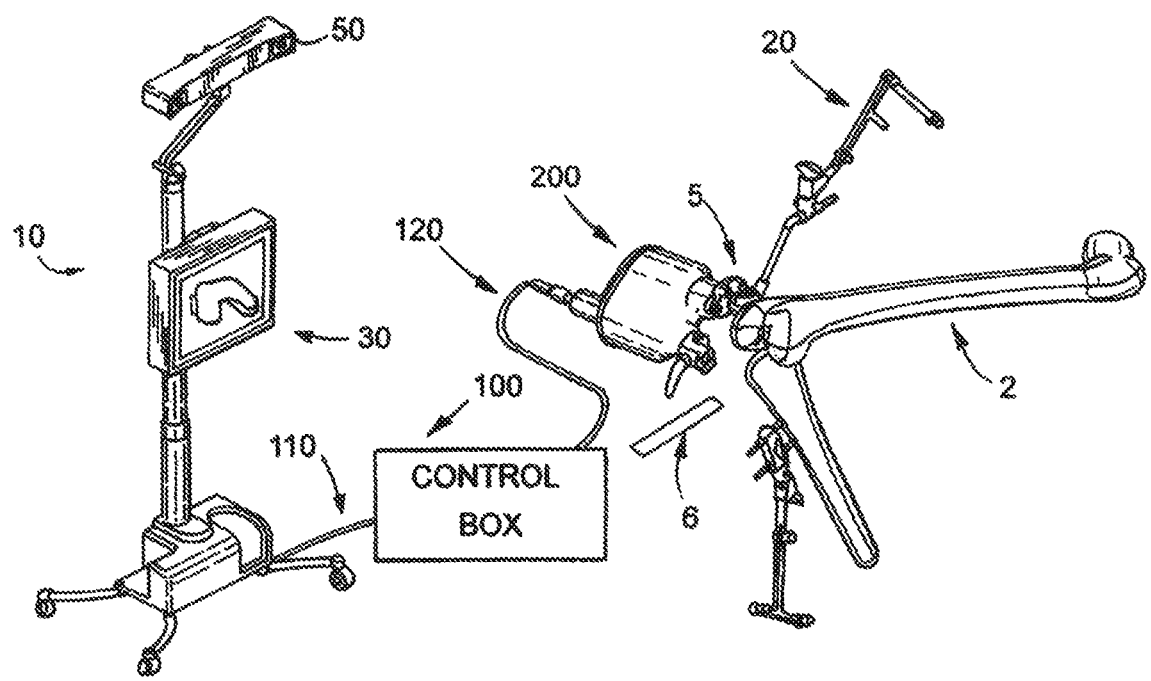
FIG. 1 is a schematic overview of a computer and robotic assisted surgical (CAS) system that includes a computer, a control box and a robot in communication with the control box.

In FIG. 1, an overview of a computer and robotic assisted surgical system (CAS) system 10, a control box (main controller) 100, and a robot 200. The CAS system 10 includes a computer (PC) 30 and preferably a position measuring system, such as an opto-electronic camera 50. The computer 30 can be any number of different types of computers including a desktop computer, laptop computer, etc.

An exemplary CAS system 10 has been described in the following patents and patent applications, which are hereby incorporated by reference in their entirety: U.S. patent application publication Nos. US2007-0106128, US2006-0161052, US2006-0200161; US2009-018445 and PCT publication No. WO2006106419. Details on the function of the robot 200 can also be found in PCT publication No. WO2006106419 entitled Robotic Guide Assembly for use in Computer-Aided Surgery.

The CAS system 10 also contains the robot controller box (main controller) 100 for interfacing with the PC 30 and the robot 200. As described below, the robot 200 includes motorized components that are operative to controllably move the robot 200. Referring to FIG. 1, the control box 100 contains a power supply for converting the main power from 120V or 240V AC to the voltage required by the motorized components of the robot (e.g., motors and controllers) (e.g. 24V). The power supply can be electrically isolated from the rest of the control box, by for example using a double insulated power supply. The control box 100 is in communication with the CAS station computer 30 via a cable 110 or the like. Several different communication protocols can be used as a means for communication between the control box and CAS station computer 30, such as USB connection protocol through a cable 110. The control box 100 preferably contains a converter box which converts the USB signal coming from the PC to a CAN bus signal (i.e. Universal Serial Bus/Controller-Area Network or USB/CAN converter). For safety, the control box 100 also contains an opto-electronic coupling which prevents high voltage or current from being erroneously delivered to the motor unit, endangering the patient or surgeon.

Figure 2:
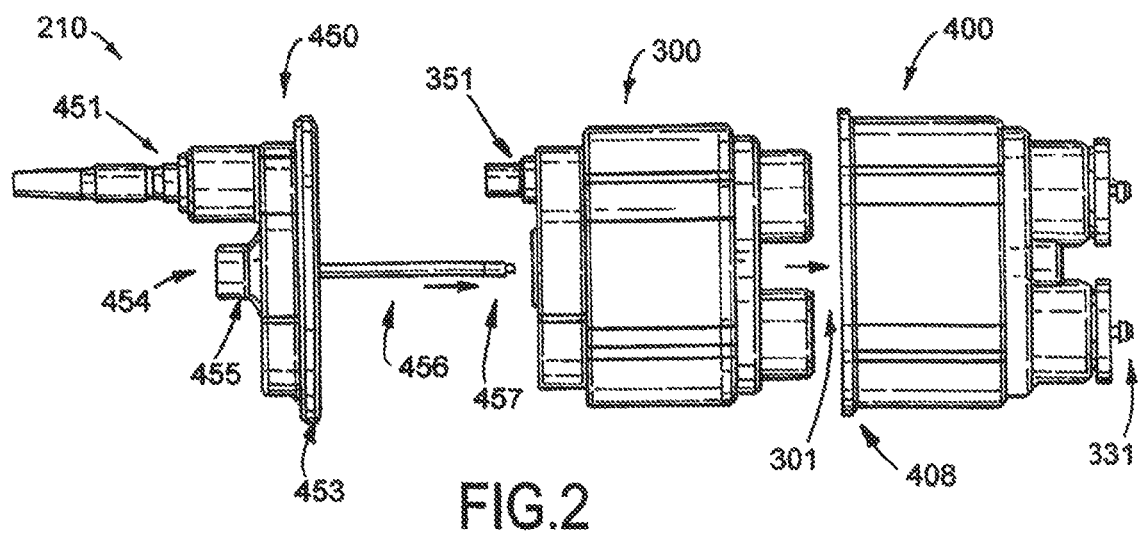
FIG. 2 is an exploded side perspective view of a motor unit and sterile enclosure that receives the motor unit.

FIG. 2 is an exploded side view of the various components that make up the motorized portion of the robot 200. FIG. 2 thus shows the robot assembly 200 in a disassembled state. The robot assembly 200 is formed of three major components, namely, a motor unit 300 and a sterile enclosure that is formed of an enclosure body or base 400 and an enclosure cover or lid 450. It will be appreciated that the three components are complementary to one another and are intended to mate with one another such that the motor unit 300 is securely and sealingly enclosed within and between the enclosure base 400 and cover 450.

Figure 3:
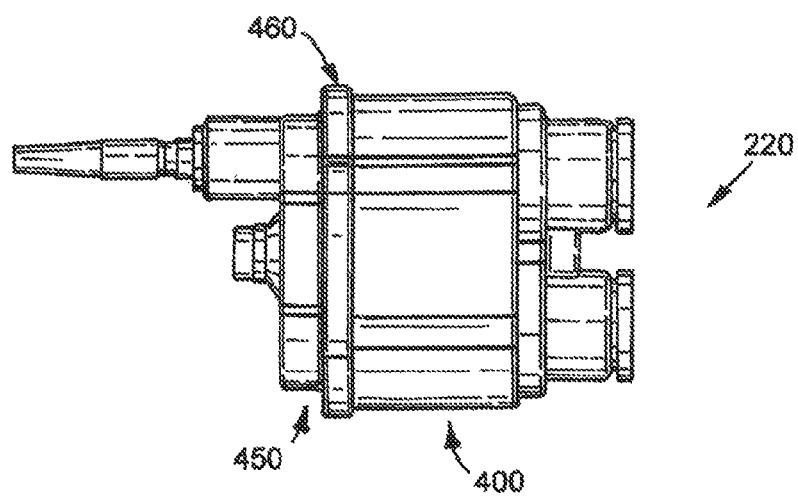
FIG. 3 is side view of the motor unit and sterile enclosure in the assembled, closed position.
Figure 4:
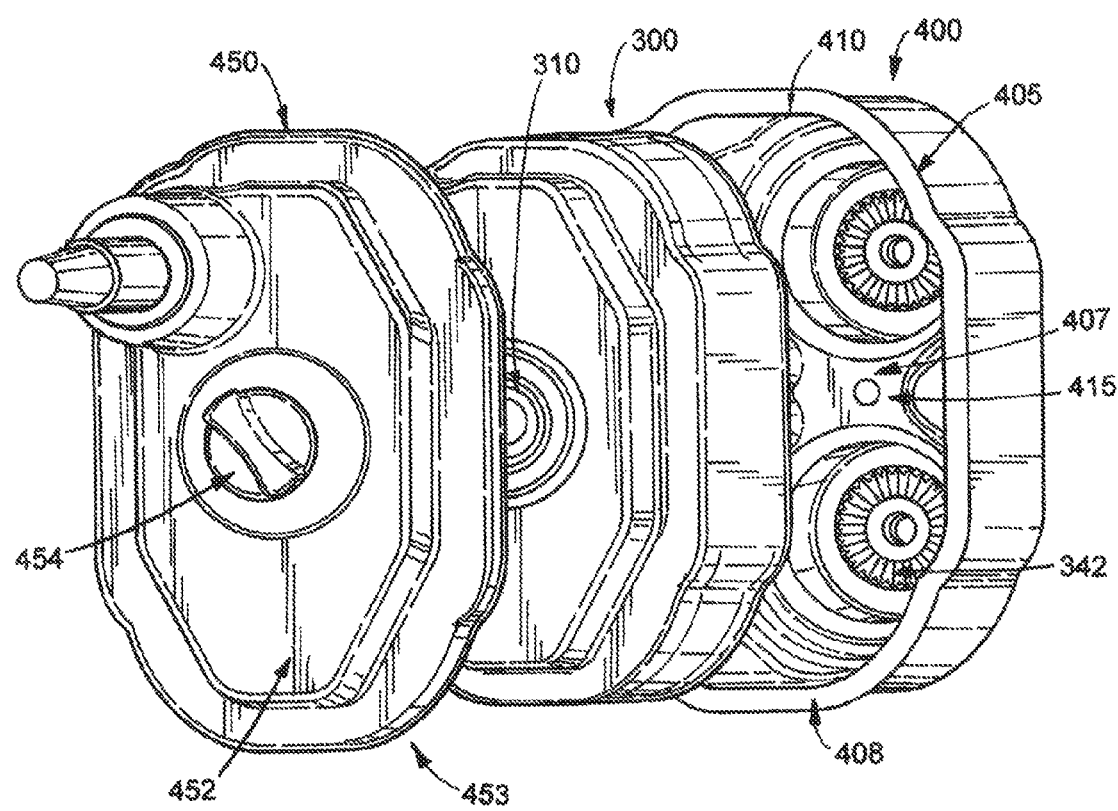
FIG. 4 is an oblique exploded perspective view of the motor unit and sterile enclosure of FIG. 2.

Referring to FIGS. 2-4, the enclosure body 400 is a hollow, cup shaped part that is defined by a side wall 405 and a floor 407 that extends between the side wall 405 at a bottom edge thereof. Since the enclosure body 400 is a hollow structure, it includes an interior compartment that is configured to receive the motor unit 300. An opening 410 at the top edge of the side wall 405 forms an entrance into the interior compartment and permits passage of the motor unit 300. The motor unit 300 fits into the enclosure body 400 by inserting the motor unit 300 in the direction along the enclosure body 400, as indicated by arrow 301. The enclosure body 400 can thus also be referred to as a shell like structure. The enclosure body 400 can have any number of different shapes, including circular, square, rectangular, irregular shaped, etc. In the illustrated embodiment, the enclosure body 400 is generally oval or oblong shaped. Additional features of the enclosure body 400 are described below.

The enclosure lid 450 is complementary to the enclosure body 400 and is designed to mate with the enclosure body 400 and seal off the interior compartment defined in the enclosure body 400, with the motor unit 300 being sealing contained within the interior compartment. The enclosure lid 450 is designed to fit over and cover the motor unit 300 and comes into contact with select portions of the enclosure body 400 when the motorized portion of the robot 200 is fully assembled as shown in FIG. 3.

When the enclosure lid 450 mates with the enclosure body 400, a tight seal 460 is formed therebetween. Any number of different mechanical attachment techniques can be used to sealingly couple the enclosure lid 450 to the enclosure body 400. For example, the top edge of the enclosure body 400 can include a flange or lip or first seal member 408 that mates with a complementary flange or lip or second seal member 453 formed along a bottom edge of the enclosure lid 450. For example, the two seal members 408, 453 can be or can include elastic members, such as a gasket or O-ring structure, that promote a seal therebetween when compressed or they can be plastic lips.

In addition, a mechanical attachment is provided for securely coupling the enclosure lid 450 to the enclosure body 400 such that the enclosure lid 450 cannot be easily removed therefrom. For example, a fastening mechanism 454 is provided to facilitate secure coupling of the enclosure body 400 and the enclosure lid 450. In one embodiment, the fastening mechanism 454 is in the form of a long central guide pin 456 that is inserted into a through-hole 310 that traverses the motor unit 300. The guide pin 456 incorporates threads 457 at its most distal end 459 that engage a threaded hole 415 that is formed in the floor 407 of the enclosure body 400.

At a proximal end of the guide pin 456, a thumb screw 455 is provided to assist the user in rotating the guide pin 456 to cause either tightening or loosening of the lid 450 relative to the enclosure body 400. Turning (rotating) the thumb screw 455 causes the guide-pin threads 457 to threadingly engage and mate with the threaded hole 415 and continued rotation causes the enclosure cover 450 to be drawn toward and into sealed engagement against the enclosure body 400, compressing the seal 465 at an interface 460 between the enclosure body 400 and lid 450. This results in the formation of a tight seal 465 between the two components.

The fastening mechanism 454 can be a part of the enclosure lid 450 or alternatively, it can be a separate part that is mated to the other parts. Since the motor unit 300 is in communication with the control box 100, both the motor unit 300 and the sterile enclosure have features to accommodate and permit such communication. For example, the motor unit 300 includes a first connector 351 that is operatively connected to the operating parts of the motor unit 300 to allow commands, signals, and other forms of communication to be both delivered to and received from the motor unit 300. The first connector 351 is located along a top of the motor unit 300 and extends outwardly therefrom. Similarly, the enclosure cover 450 includes a second connector 451 that is configured to operatively mate with the first connector 351 when the motor unit 300 is contained with the sterile enclosure. The combined connectors 351, 451 serve to connect the motor unit 300 to the control box 100 via the robot cable 120.

The connectors 351, 451 can also serve as a guide for the rotational alignment of the enclosure cover 450 about the long axis of the guide pin 456 with respect to the motor unit 300 during the closing of the enclosure body 400 and cover 450. The connectors 351, 451 are positioned such that when the enclosure cover 450 is fully closed the two connectors 351 and 451 are in contact and the electrical signal connection is completed. While the electrical connector is described herein as being formed of two connectors, it will be understood that it can be in the form of a single connector that is formed of two connector portions.

The robot cable 120 can be hardwired to the enclosure lid connector 451 or attached via a detachable connector.

Figure 5:
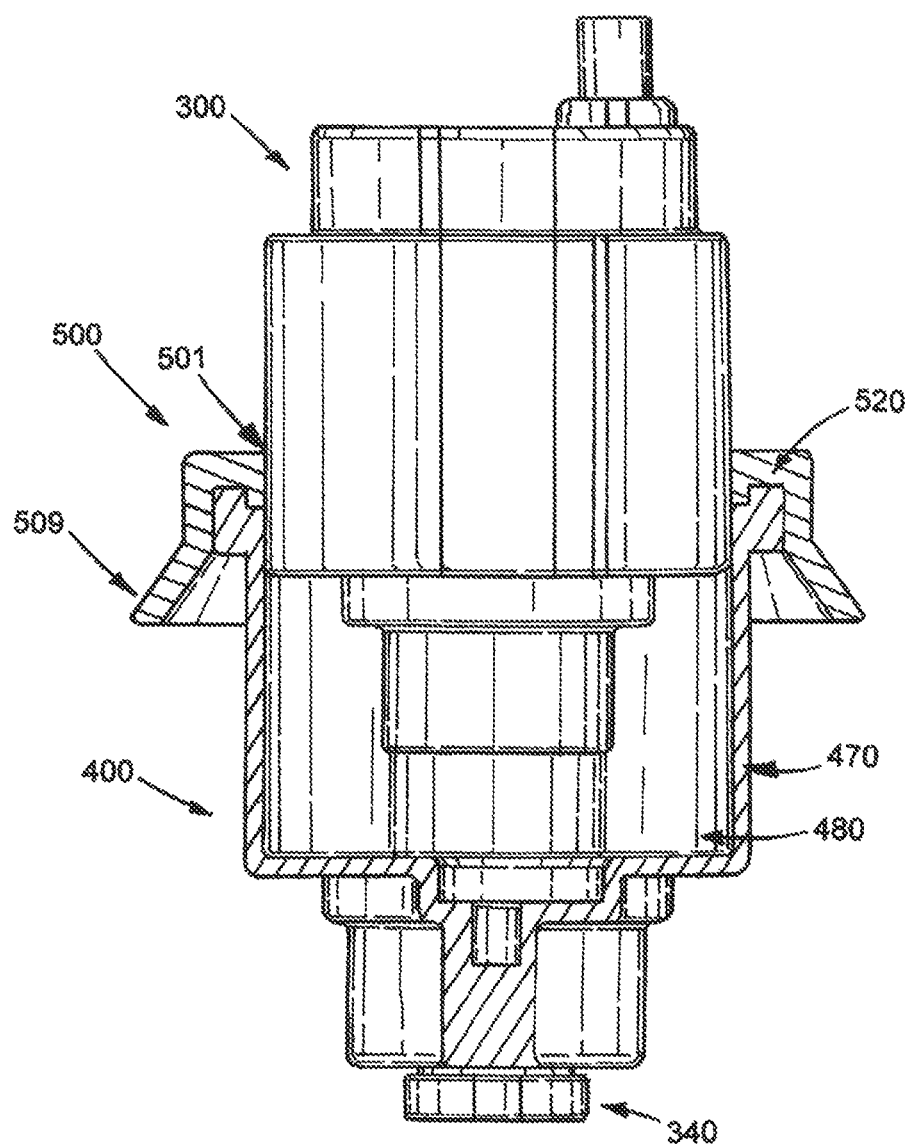
FIG. 5 is a cross-sectional side view of an enclosure body of the sterile enclosure and insertion guide, and the motor unit.

Referring now to FIG. 5, a cross-sectional view of the enclosure body 400 and an insertion guide 500 is shown. In accordance with the present invention, the insertion guide 500, enclosure body 400 and enclosure cover 450 are sterile components free of any bacteria or contamination. These components 500, 400, 450 can be cleaned and sterilized using typical medical sterilization procedures such as steam sterilization in an autoclave, ETO or gas sterilization, or any other known means. Some suitable polymer materials for manufacturing a sterilizable (autoclavable) enclosure include polyoxymethylene (POM) and Radel® polyphenylsulfone.

Alternatively, these components 500, 400, 450 can be packaged and delivered sterile from the manufacturer and be of a single use and therefore are discarded after use. The enclosure body 400 and enclosure cover 450 can be manufactured using methods that result in low production costs (e.g., manufacturing out of plastic by an injection molding process).

As shown in FIG. 5, the enclosure body 400 has an inner surface 480 and an outer surface 470. The outer surface 470 is intended to remain sterile during the surgery while the inner surface 480 is intended to be in contact with or in close proximity to the non sterile motor unit 300. Thus, once the motor unit 300 is inserted into the enclosure body the inner surface 480 can also be considered non sterile. The insertion guide 500 serves as a sterile shield that prevents contamination of the lip 408 of the enclosure body 400 and the outer surface 470. The insertion guide 500 has a body that includes a central opening 501 through which the motor unit 300 can be received and has an inner surface that is configured to mate with the enclosure body 400 and in particular, the lip 408 thereof. The inner surface can includes a channel or recessed section 520 that receives the lip 408 and thereby sealingly mate and couple the shield 500 to the enclosure body 400. For recessed channel 520 thus has a footprint that has the same shape as the lip 408 (e.g., oval shaped recessed channel).

The shield 500 can have a flared side and end 509 that surrounds the outer surface 470 of the enclosure body 400. The flared or outward extending sides of the shield increases the shielded area in the horizontal plane when the enclosure is in the vertical position and the motor unit is being inserted, thereby increasing the area of protection over the enclosure and reducing the risk of contaminating the external surface of the enclosure body. It will be understood that the shield 500 is intended to be used only temporarily while the motor unit 300 is being inserted into the enclosure body 400.

One exemplary process for assembling the motor unit 300 into the enclosure follows an aseptic transfer process. Before each surgery, the insertion guide 500, enclosure body 400 and cover 450 are provided sterile (either provided and packaged sterile by the manufacturer or sterilized before the procedure by the hospital). The motor unit 300 is typically not sterile, and needs to be inserted into the sterile enclosure defined by the enclosure body 400 and cover 450. The aseptic transfer process requires two persons, one sterile and one non-sterile, with the sterile person being properly gloved, gowned and capped. The sterile person holds the enclosure body 400 in an upright position as shown in FIG. 5 with the enclosure opening 410 facing up and the robot axes (longitudinal axes) facing down. The sterile person picks up the sterile insertion guide 500 and places it on the lip 408 of the enclosure body 400. The non-sterile person than inserts the motor unit 300 into the enclosure body 400 from above, centering the motor unit 300 over the enclosure opening 410 and sliding or dropping it into the enclosure body 400.

The non-sterile person then lifts the insertion guide 500 off of the enclosure body 400 and removes it from the sterile field. The interior surface 480 of the enclosure body 400 is now considered contaminated while the exterior surface 470 remains sterile. The sterile person then picks up the enclosure cover 450 and closes the enclosure body 400 by inserting the central guide pin 456 of the cover 450 down the through hole 310 of the motor unit 300 and into the hole 415 of the enclosure body 400. The sterile person then tightens the thumb screw, thereby engaging and tightening the enclosure cover 450 over the enclosure body 400 and sealing the motor unit 300 completely inside the enclosure. As previously mentioned, gaskets or O-rings, static seals, dynamic seals, lip seals, spring seals or any other types of seals can be used to insure a good sealing between the components that form the motorized components of the robot. Seals are preferably also incorporated around the moving parts of the enclosure body, including seals 371, 381 (FIG. 6) associated with the enclosure output shafts 330, 340, and seals 391 associated with the output axes screws 331. It will be appreciated that the outer surface 470 of the enclosure body 400 and the outer surface 451 of the enclosure cover 450 remain sterile while the respective inner surfaces 480 and 452 are non-sterile. The sterile person then tightens output axes screws 331 and 341 that are associated with the enclosure body 400 (as described below) in order to couple output shafts 330 and 340 to their respective motor unit shafts 335 and 345 that are contained within the motor unit 300.

The motor unit 300, enclosure body 400, and enclosure cover 450 are preferably asymmetrical or have an asymmetrical feature that allows the motor unit to be inserted into the enclosure body 400 and the enclosure cover 450 to be assembled on the enclosure body 400 in only one unique direction. For example, as can be seen in FIG. 7, the perimeter of the motor unit 300 can be asymmetrical about the two motor axes, making it impossible to insert the motor unit in more than one manner. This assures that a first motor 610 (FIG. 6) is always coupled to the first output shaft 340 that extends along one axis of the enclosure and a second motor 620 (FIG. 6) is always coupled to the second output shaft 330 that extends along another axis of the enclosure when assembled. As described in more detail herein, the motor unit 300 thus includes one or more motors and preferably at least two motors. In the illustrated embodiment, the motor unit 300 includes two motors, namely, the first and second motors 610, 620. Each motor has its own drive shaft.

Each motor unit shaft has an interface for coupling to the output shafts 330, 340 of the enclosure. As can be seen in FIGS. 4 and 7, the interface is preferably made up of a plurality of teeth 342 and 346, respectively, arranged radially from the center and allowing engagement of the respective motor shafts at any angle. However, any mechanical coupling system known in the art that can be used as a coupling interface that is configured for use in the present invention. Exemplary mechanical coupling systems can include pins that engage into holes or with other surfaces, figure or notch joints, etc.

Once the enclosure is closed, any attachments to be positioned or manipulated by the robot assembly (such as bone fixation devices 5 or surgical cutting guides to be positioned relative to bones 2) can be installed to the output shafts 330 and 340 of the enclosure, and the robot 200 is assembled and ready to use for the surgeon. Alternatively these attachments may be attached to the enclosure before assembly, or they may be integral to the enclosure output axes. The robot cable 120 if detachable from the enclosure can also be attached to the connector either before or after assembly.

Figure 6:
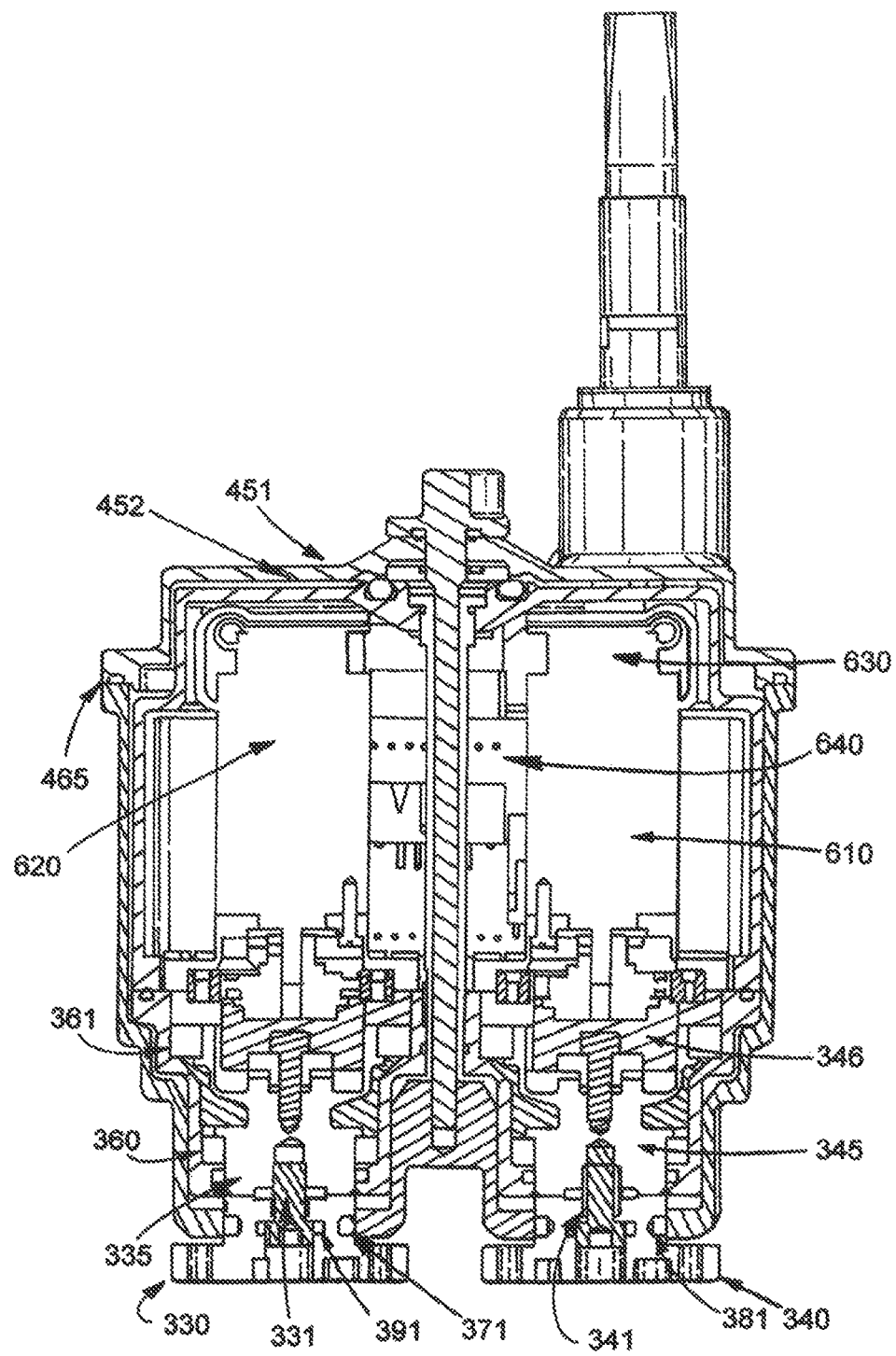
FIG. 6 is a cross-sectional view of the sterile enclosure and the motor unit when assembled.
Figure 7:
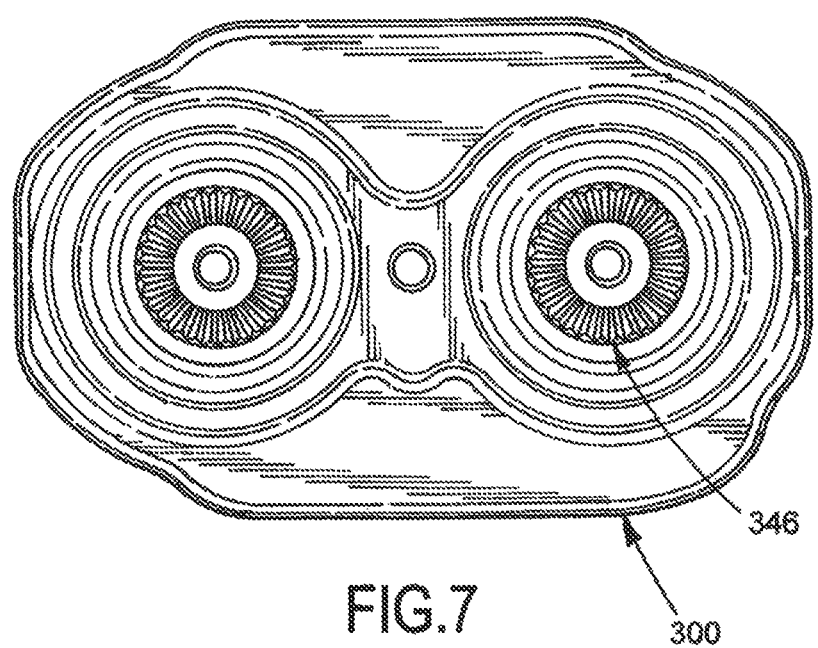
FIG. 7 is a bottom plan view of the motor unit.

The components of the motor unit 300 can be best viewed in the cross-sectional view FIG. 6. As described above, the motor unit 300 includes at least one and preferably two or more motors. The illustrated motor unit 300 contains motors 610, 620, and preferably includes other working components that are operatively connected to the motors 610, 620 to ensure the proper operation thereof. In one embodiment, the motor unit 300 includes hall sensors, encoders 630, and the motor controllers 640.

Suitable types of motors 610, 620 and motor (motion) controllers 640 are provided by several known manufactures, including but not limited to Maxon/EPOS and Faulhaber (MCLB 3006 CAN). As is known, a hall sensor is a transducer that varies its output voltage in response to changes in magnetic field. Hall sensors are often used for proximity switching, positioning, speed detection and current sensing applications. The Maxon/EPOS device is a digital motion controller capable of position, velocity, and current mode. In addition, the EPOS device also accepts external signals to operate in "Step & Direction" mode or "Master Encoder" mode ("electronic gearbox"). The small package size and cost-efficient design makes the EPOS an attractive choice for controlling brush or brushless motors. An encoder is generally a device, circuit, transducer, software program, algorithm or person that converts information from one format or code to another, for the purposes of standardization, speed, secrecy, security, or saving space by shrinking size.

The motors 610, 620 are preferably brushless motors with hall sensors being used for communication, and the encoders 630 being used for position measurement. The hall sensors can also serve as a redundant position measuring system. The controllers 640 are connected to each motor 610, 620 with 8 wires and to each encoder 630 with 5 wires. Encoders 630 can be optical or magnetic, and can be integral with the motors 610, 620.

In contrast to conventional robot and motor arrangement, the present invention includes a compact motor unit 300 that includes not only the motors 610, 620 but also includes other operative parts that complement the motors 610, 620. More specifically, an advantage of having the motor's controllers 640 directly inside the motor unit 300 instead of in the control box 100 (as in the conventional configuration) is that the connection between the motors 610, 620 and controllers 640 can be very short (on the order of a few centimeters) as opposed to having to route the connections through a long cable, such as cable 120 that connects the box 100. This greatly reduces the susceptibility to electromagnetic noise that can interfere with the motion control commands coming from the controllers 640 and going to the encoders 630 and hall sensors.

The cable 120 which connects the control box 100 with the robot 200 and motor unit 300 is preferably a long cable, about 3 or 5 meters due to the position of the CAS station in the operating room. A second advantage of having the motor controllers 640 directly inside the motor unit 300 instead of in the control box 100 is that the connection between the controllers 640 and the control box 100 can be a simple cable made up of only 4 wires, instead of 16 or more wires which would be required to drive two motors 610, 620 and communicate with the hall sensors (plus additional wires required for the encoder 630 or redundant system). Thus, the cable 120 can be relatively inexpensive to manufacture and be made for single use. This avoids having to sterilize the cable, and risk damaging it and rendering the system less reliable. The motor unit also contains gears, preferably harmonic drive gears 346, and shafts 335 that interface with the enclosure. The shafts are supported by bearings 360, 361, for providing smooth and accurate positioning qualities. Including the motors 610, 620, controllers 640, gears, and axes with support bearings in the motor unit 300 results in a minimum of components required for the enclosure, making it simple and inexpensive to manufacture and provide as a single use component. The support bearings could also be included on the output shafts 330, 340, of the enclosure. However, incorporating the bearings that provide accurate positioning, orientation and rotation of the output shafts of the robot into the motor unit is preferable for a number of reasons. Firstly, the motor unit is not sterilized and therefore the bearings are not subjected to the harsh chemicals, steam, temperatures and other environmental conditions. Secondly, accurate bearing systems such as ball bearings are preferably lubricated, and are typically difficult to clean. This could affect sterility if they were housed in the sterile enclosure body. Thirdly, incorporating the bearings into the motor unit allows for a simplified coupling interface between the output shafts of the motor and the enclosure body. In particular, it allows the shafts 330, 340 of the enclosure body to be slightly mobile or 'free-floating' so that the enclosure shafts do not need to be very accurately positioned with respect to the enclosure body 400 (their position and orientation become accurately fixed once they are coupled to the output axes 335, 345, of the motor unit using the fixation screws 331, 341). Therefore, once the output shafts of the enclosure are rigidly coupled to the output shafts of the motor unit, the output shafts of the enclosure rotate about the rotational axes defined by the support bearings in the motor unit, which are accurate to a high degree. Any misalignment between the rotational axes of the motor unit shafts and the enclosure shafts is taken-up or compensated for by the slight mobility of the enclosure output shafts. This also allows the elastic seal members 371, 381, of the enclosure output shafts 330, 340 to be used both as the supports for 'mobile' enclosure output shafts 330, 340 within the enclosure body, as well as providing a sealing function, thereby necessitating a minimum of parts and further simplifying the enclosure body, making it easy to manufacture, clean, sterilize, and to provide as a single use component.

One of the advantages of the current invention is that it offers a more reliable and robust control structure and position control feedback loop. The computer sends a positioning command from the PC 30 to the control box 100 via the USB cable 110 and communication protocol. This USB protocol is then converted to a CAN bus signal using the USB-to-CAN converter and sent to the controllers 640 in the motor unit 300 via the robot cable 120. The motion controllers 640 in the motor unit then convert the CAN bus position signal to low level hall sensor communication pulses and motor phase signals, and command the motors 610, 620 under servo control to move to the desired position. The encoders 630 and/or hall sensors are reading and monitoring the position of the motors and sending this information back the controllers 640. The controllers 640 maintain a local control loop with the motors 610, 620, controlling the motor position or motor torque as required. The controllers 640 decode the signals from the motors 610, 620, and send back information to the control box 100 via the CAN-bus. This information is then sent back to the PC via USB signal. The USB signal is preferably checked for data integrity with an error detecting code such as a cyclical redundancy check (CRC) function.

In an alternative embodiment of the invention the communication from the PC to the CAN-bus is realized using a CAN-bus network interface card inserted directly into a PCI slot of the motherboard of the PC 30. This would avoid having to use a USB interface altogether for communicating to the control box 100, making for an even simpler and more reliable system.

The position measurement system 50 can simultaneously monitor the position of the robot 200 via references or rigid body arrays. As shown in FIG. 1, a reference array 'F' 20 can be attached to the bone 2 and to the robot axis output via the fixation system 5. Reference arrays can also be attached directly to the robot enclosure or to the other output axis or instruments, cutting guides, etc. . . . that are attached to the other robot axes (not shown). This position data is sent to the PC 30, and can be used to calibrate and register and check the position of the robot 200. These data can also be displayed to the surgeon on the screen of the CAS station. As mentioned previously, the CAS system including the position measurement system, reference arrays or markers, as well as the guiding instrumentation, cutting tools, bone fixations, etc. . . . have been previously described, such as in PCT publication No. WO2006106419 entitled Robotic Guide Assembly for use in Computer-Aided Surgery which has been incorporated by reference in its entirety.

The described system provides increased reliability and safety for intra-operative robot positioning systems. The system also has a longer lifespan because none of the electronic components need be sterilized in an autoclave or other harsh chemicals.

There are a number of alternative embodiments of the system described herein. For example, the motor unit may include a battery and wireless communication to avoid having to connect the robot with a cable.

The enclosure cover can be permanently attached to enclosure body. Instead using a linear sliding motion to close the cover, closing of the enclosure can be achieved using a rotational motion of the cover, for example about a hinge that connects the enclosure cover to the enclosure body.

What is claimed is:

1. A robotic assisted surgical system comprising:
a computer;
a robot;
a main controller in communication with the computer and the robot; and
a motor unit assembly that is associated with the robot and is in communication with the main controller, the motor unit assembly having:
 a non-sterile motor unit that includes at least one motor and a motor controller that is operatively connected to the at least one motor, and
 a sterile enclosure that surrounds and contains the non-sterile motor unit, the sterile enclosure including:
  first and second parts that are detachable from one another in which each part includes a sterile outer surface, while an inner surface of each part is non-sterile due to the presence of the non-sterile motor unit, the first part being a hollow enclosure base that receives the non-sterile motor unit and includes a first seal member at one end thereof and the second part being an enclosure cover that mates with the enclosure base for capturing the non-sterile motor unit therebetween, the enclosure cover having a second seal member that mates with the first seal member for providing a seal,
 wherein the non-sterile motor unit, enclosure base and enclosure cover have an asymmetrical feature that allows the non-sterile motor unit to be inserted into the enclosure base in only one unique direction and the enclosure cover to be assembled on the enclosure base in only one unique direction.

2. The system of claim 1, wherein the non-sterile motor unit includes a pair of motors each of which has a drive shaft and the enclosure includes a pair of output shafts that are coupled to the drive shaft of the pair of motors when the non-sterile motor unit is in a fully assembled position within the enclosure.

3. The system of claim 2, wherein the enclosure includes an interface for coupling the pair of motors to the output shafts of the enclosure, the interface permitting engagement of the respective drive shafts of the pair of motors regardless of an angular position of the drive shafts.

4. The system of claim 1, wherein the non-sterile motor unit includes a first connector and the enclosure includes a second connector that mates with the first connector when the enclosure is sealed, wherein the second connector is attached to the main controller with a cable.

5. The system of claim 1, wherein the non-sterile motor unit includes a battery and is in wireless communication with the robot.

6. A surgical robotic system comprising:
a motor unit assembly that is associated with a robot for use in a sterile surgical field, the motor unit assembly having:
 a non-sterile motor unit that includes a pair of motors each of which has a drive shaft and a motor controller;
 a sterile enclosure that surrounds and contains the non-sterile motor unit, the sterile enclosure including a pair of output shafts that are coupled to the drive shafts of the pair of motors when the non-sterile motor unit is in a fully assembled position within the enclosure; and
 an interface for coupling the non-sterile motor unit to the output shafts of the enclosure, the interface including a plurality of teeth arranged radially for allowing engagement of the respective output shafts at any angle, and wherein the interface permits engagement of the respective drive shafts of the pair of motors regardless of an angular position of the drive shafts.

7. A surgical robotic system comprising:
a motor unit assembly that is associated with a robot for use in a sterile surgical field, the motor unit assembly including:
 a non-sterile motor unit having at least one motor and a motor controller, and
 a sterile enclosure that surrounds and contains the non-sterile motor unit, the sterile enclosure including:
  first and second parts that are detachable from one another in which each part includes a sterile outer surface, while an inner surface of each part is non-sterile due to the presence of the non-sterile motor unit, the first part being a hollow enclosure base that receives the non-sterile motor unit and includes a first seal member at one end thereof and the second part being an enclosure cover that mates with the enclosure base for capturing the non-sterile motor unit therebetween, the enclosure cover having a second seal member that mates with the first seal member for providing a seal,
 wherein the non-sterile motor unit, enclosure base and enclosure cover have an asymmetrical feature that allows the non-sterile motor unit to be inserted into the enclosure base in only one unique direction and the enclosure cover to be assembled on the enclosure base in only one unique direction.

8. A surgical robotic system comprising:
a motor unit assembly that is associated with a robot for use in a sterile surgical field, the motor unit assembly including:
a non-sterile motor unit having at least one motor and a motor controller, and
a sterile enclosure that surrounds and contains the non-sterile motor unit,
wherein the non-sterile motor unit includes gears and shafts that interface with the sterile enclosure and are supported by bearings, thereby providing smooth and accurate positioning qualities, and
wherein the non-sterile motor unit includes at least one accurately supported output shaft that is coupled with at least one floating enclosure output shaft, whereby after coupling the enclosure output shaft rotates about rotational axes of the accurately supported non-sterile motor unit output shaft.

9. The surgical robotic system of claim 7, wherein the motor unit assembly further includes an insertion guide having a central opening for receiving the non-sterile motor unit therethrough and mates with one of the first and second parts of the sterile enclosure.

10. The system of claim 1, wherein the motor unit assembly further includes an insertion guide having a central opening for receiving the passage of the non-sterile motor unit therethrough and mates with a lip of the first part of the sterile enclosure.

11. The surgical robotic system of claim 6, wherein the non-sterile motor unit includes a first connector and the sterile enclosure includes a second connector that mates with the first connector for operatively connecting the non-sterile motor unit to a main controller via a cable.

12. The surgical robotic system of claim 6, wherein the non-sterile motor unit includes hall sensors for communication encoders for position measurement, the motor controller being connected to the at least one motor.

13. The surgical robotic system of claim 8, wherein the non-sterile motor unit includes a pair of motors each of which has a drive shaft and the enclosure includes a pair of output shafts that are coupled to the drive shaft of each of the pair of motors when the non-sterile motor unit is in a fully assembled position within the enclosure.

14. The surgical robotic system of claim 13, wherein the enclosure includes an interface for coupling the pair of motors to the output shafts of the enclosure, the interface permitting engagement of the respective drive shafts of the pair of motors regardless of an angular position of the drive shafts.

15. The surgical robotic system of claim 14, wherein the interface comprises a plurality of teeth arranged radially for allowing engagement of the respective drive shafts at any angle.

16. The surgical robotic system of claim 8, wherein the non-sterile motor unit includes a first connector and the sterile enclosure includes a second connector that mates with the first connector for operatively connecting the non-sterile motor unit to a main controller via a cable.

17. The surgical robotic system of claim 8, wherein the non-sterile motor unit includes hall sensors for communication encoders for position measurement, the motor controller being connected to the at least one motor.

18. The surgical robotic system of claim 7, wherein one of the first and second seal members is a flange or a lip and the other of the first and second seal members is an elastic member, gasket or O-ring.

19. The surgical robotic system of claim 7, wherein each of the first and second seal members is a flange, a lip, an elastic member, a gasket or an O-ring.

20. The surgical robotic system of claim 7, wherein the non-sterile motor unit includes a pair of motors each of which has a drive shaft and the enclosure includes a pair of output shafts that are coupled to the drive shaft of each of the pair of motors when the non-sterile motor unit is in a fully assembled position within the enclosure.

21. The surgical robotic system of claim 20, wherein the enclosure includes an interface for coupling the the pair of motors to the output shafts of the enclosure, the interface permitting engagement of the respective drive shafts of the pair of motors regardless of an angular position of the drive shafts.

22. The surgical robotic system of claim 21, wherein the interface comprises a plurality of teeth for allowing engagement of the respective drive shafts of the pair of motors at any angle.

23. The surgical robotic system of claim 7, wherein the non-sterile motor unit includes a first connector and the enclosure cover includes a second connector that mates with the first connector for operatively connecting the non-sterile motor unit to a main controller via a cable.

24. The surgical robotic system of claim 7, wherein the non-sterile motor unit includes hall sensors for communication encoders for position measurement, the motor controller being connected to the at least one motor.

25. The surgical robotic system of claim 23, wherein a connection between the at least one motor and the respective motor controller is fully contained within the enclosure and is remote from the main controller.

26. The surgical robotic system of claim 7, further comprising a computer assisted surgical system that includes a computer that is configured to send a positioning command from the computer to a main controller in communication with the motor unit assembly via a first cable and according to a first communication protocol, wherein the first communication protocol is converted into a first signal using a converter, the first signal being delivered to the motor controller that is located in the non-sterile motor unit via a second cable.

27. The surgical robotic system of claim 26, wherein the motor controller in the non-sterile motor unit converts the signal to a low level second signal that commands the at least one motor to move to a desired position.

28. The surgical robotic system of claim 27, wherein the first cable comprises a USB cable, the first communication protocol comprises USB protocol, the first signal comprises CAN bus signal, the converter comprises a USB-to-CAN converter, and the second signal comprises low level hall sensor communication pulses and motor phase signals.

29. The surgical robotic system of claim 7, wherein the non-sterile motor unit contains gears and shafts contained within the non-sterile motor unit which interface with the enclosure and are supported by bearings, thereby providing smooth and accurate positioning qualities.

30. The surgical robotic system of claim 29, wherein the non-sterile motor unit contains at least one accurately supported output shaft that is coupled to at least one floating enclosure output shaft, whereby after coupling the enclosure output shaft rotates about rotational axes of the accurately supported motor unit output shaft.

* * * * *